(12) United States Patent
Oskin et al.

(10) Patent No.: US 8,409,110 B2
(45) Date of Patent: Apr. 2, 2013

(54) THERMAL MONITORING

(75) Inventors: Christopher L. Oskin, Grafton, MA (US); Brian M. Hanley, Framingham, MA (US); Michael Barenboym, Framingham, MA (US)

(73) Assignee: Medifocus, Inc., Columbia, MD (US)

( * ) Notice: Subject to any disclaimer, the term of this patent is extended or adjusted under 35 U.S.C. 154(b) by 337 days.

(21) Appl. No.: 12/238,589

(22) Filed: Sep. 26, 2008

(65) Prior Publication Data
US 2009/0093733 A1 Apr. 9, 2009

Related U.S. Application Data

(60) Provisional application No. 60/977,878, filed on Oct. 5, 2007.

(51) Int. Cl.
*A61B 5/00* (2006.01)
*G01K 1/00* (2006.01)
*G01K 13/12* (2006.01)
*G01K 1/08* (2006.01)

(52) U.S. Cl. .................. 600/549; 374/100; 374/158

(58) Field of Classification Search .................. 600/549; 606/31; 607/102, 138; 374/100, 158, 208, 374/209
See application file for complete search history.

(56) References Cited

U.S. PATENT DOCUMENTS

| | | | |
|---|---|---|---|
| 4,046,139 A | 9/1977 | Horn | |
| 5,335,669 A * | 8/1994 | Tihon et al. | 600/549 |
| 5,385,544 A | 1/1995 | Edwards et al. | |
| 5,404,881 A * | 4/1995 | Cathaud et al. | 600/427 |
| 5,540,655 A | 7/1996 | Edwards et al. | |
| 5,666,954 A | 9/1997 | Chapelon et al. | |
| 5,792,070 A * | 8/1998 | Kauphusman et al. | 600/549 |
| 5,865,788 A | 2/1999 | Edwards et al. | |
| 6,009,351 A | 12/1999 | Flachman | |
| 6,142,993 A | 11/2000 | Whayne et al. | |
| 6,348,039 B1 * | 2/2002 | Flachman et al. | 600/549 |
| 6,402,742 B1 | 6/2002 | Blewett et al. | |
| 6,419,653 B2 | 7/2002 | Edwards et al. | |
| 6,475,140 B1 | 11/2002 | Konstorum et al. | |
| 6,477,426 B1 | 11/2002 | Fenn et al. | |
| 6,490,488 B1 | 12/2002 | Rudie et al. | |
| 6,592,579 B2 | 7/2003 | Arndt et al. | |

(Continued)

FOREIGN PATENT DOCUMENTS

WO    WO 2007/044114 A2    4/2007

OTHER PUBLICATIONS

Notification of Transmittal of the International Search Report and the Written Opinion of the International Searching Authority, or the Declaration mailed Feb. 6, 2009 for corresponding International Application No. PCT/US2008/077772.

*Primary Examiner* — Sean P Dougherty
*Assistant Examiner* — Devin Henson
(74) *Attorney, Agent, or Firm* — Merek, Blackmon & Voorhees, LLC

(57) ABSTRACT

A rectal thermal monitor for transrectal prostate temperature measurement includes a handle arranged in a proximal end portion of the monitor for gripping by a user, an elongate shaft extending from the handle, and a probe portion arranged on a distal end portion of the shaft. The probe portion is arranged at a position opposite the handle portion, and is shaped to facilitate insertion through an anal sphincter and into a rectum of a patient. A temperature sensing element is arranged within the distal probe portion and is adapted and configured to sense a temperature of the prostate of the patient through the rectum wall of the patient. The probe portion can include one or more compliant materials and/or be shaped so as to compress during insertion through the anal sphincter of the patient.

22 Claims, 12 Drawing Sheets

U.S. PATENT DOCUMENTS

| | | |
|---|---|---|
| 6,610,054 B1 | 8/2003 | Edwards et al. |
| 6,743,226 B2 | 6/2004 | Cosman et al. |
| 6,788,977 B2 | 9/2004 | Fenn et al. |
| 6,814,712 B1 | 11/2004 | Edwards et al. |
| 6,824,516 B2 | 11/2004 | Batten et al. |
| 6,852,091 B2 | 2/2005 | Edwards et al. |
| 6,868,290 B2 | 3/2005 | Bolmsjö |
| 6,895,282 B2 | 5/2005 | Gellman et al. |
| 7,036,984 B2 * | 5/2006 | Penney et al. ............... 374/208 |
| 7,374,336 B2 * | 5/2008 | Fraden ...................... 374/208 |
| 7,422,367 B2 * | 9/2008 | Howansky .................. 374/208 |
| 2005/0281314 A1 | 12/2005 | Fraden |
| 2007/0047618 A1 | 3/2007 | Howanski |
| 2007/0093880 A1 * | 4/2007 | Reever ....................... 607/100 |

* cited by examiner

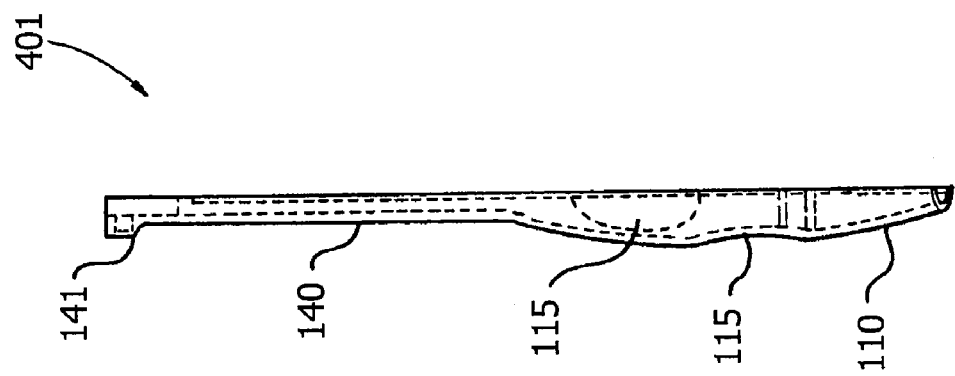
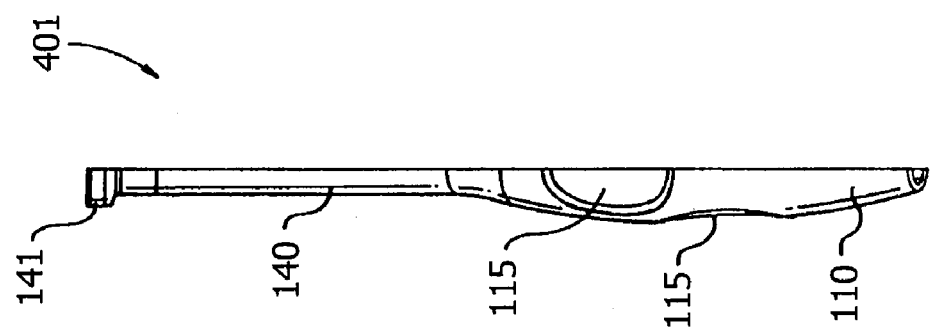

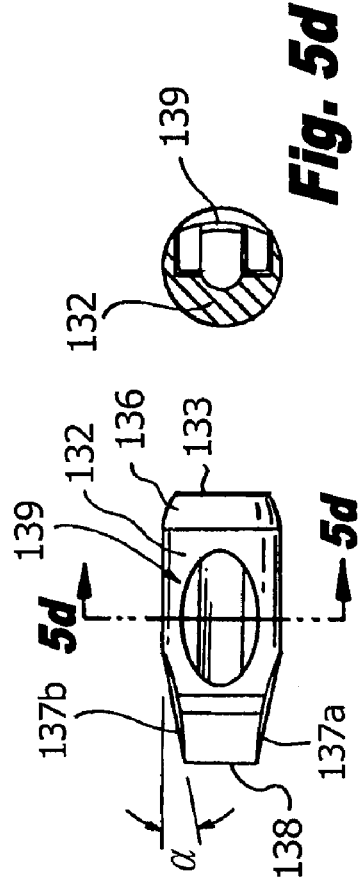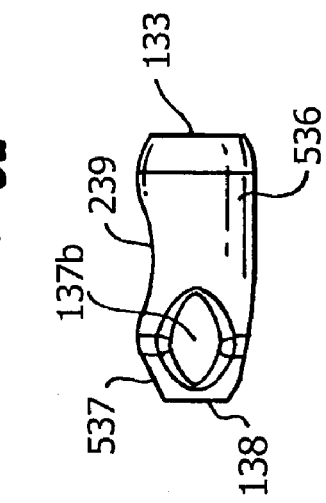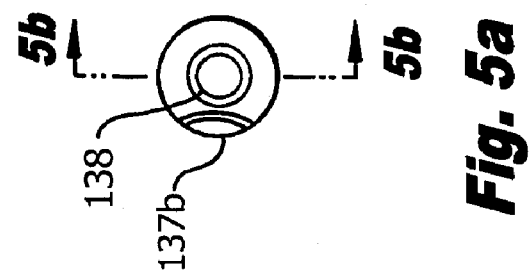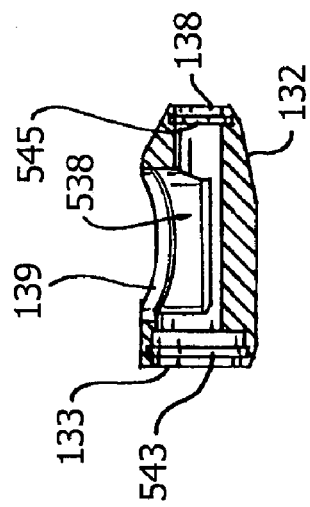

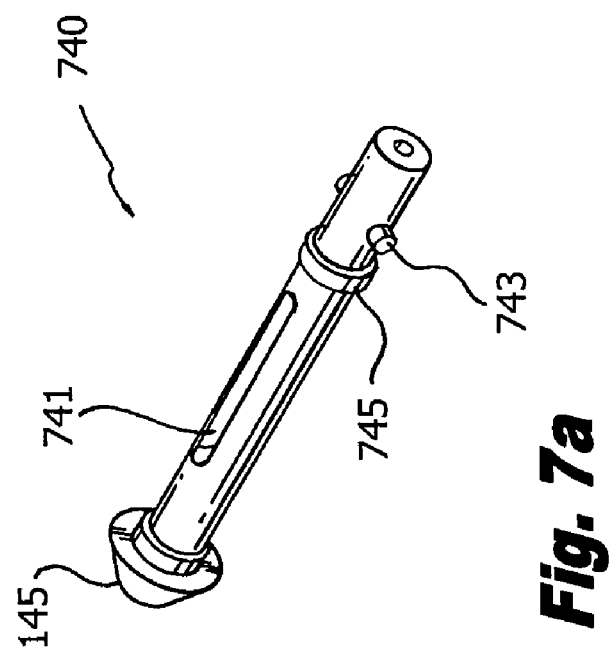
Fig. 7a
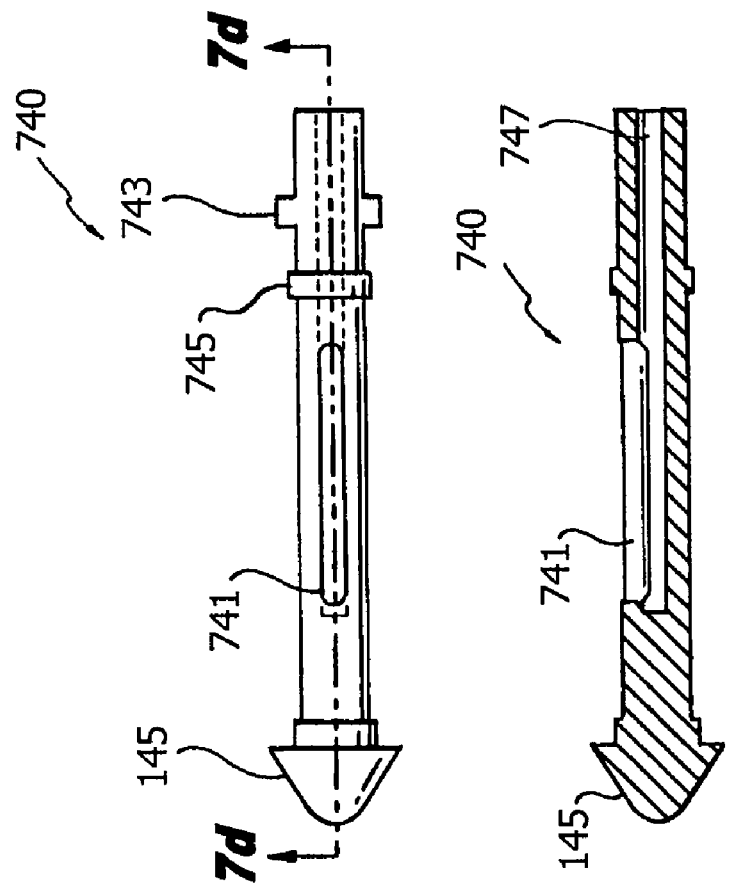
Fig. 7b
Fig. 7c

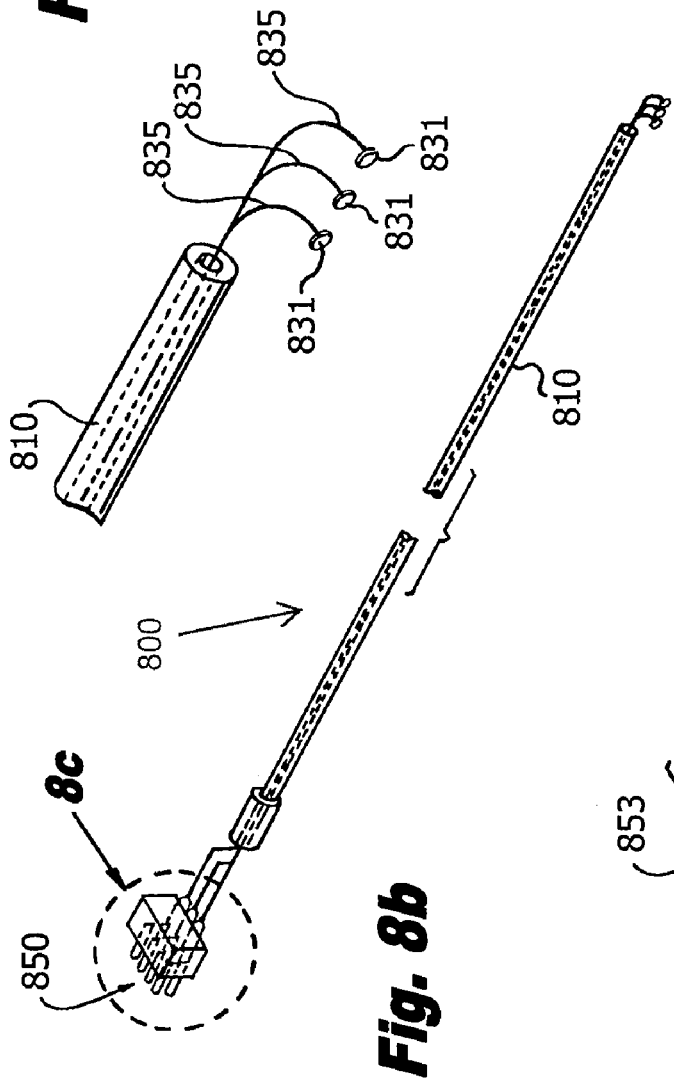
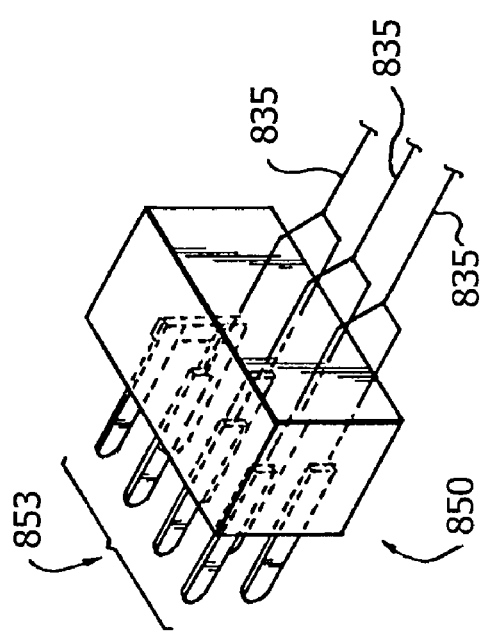

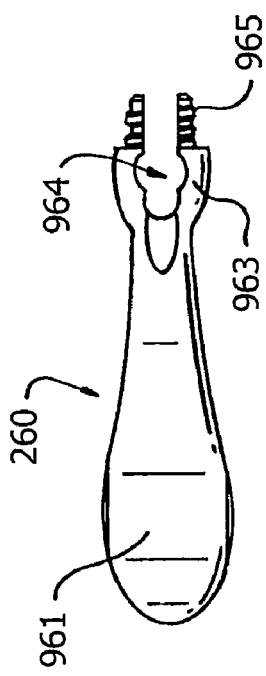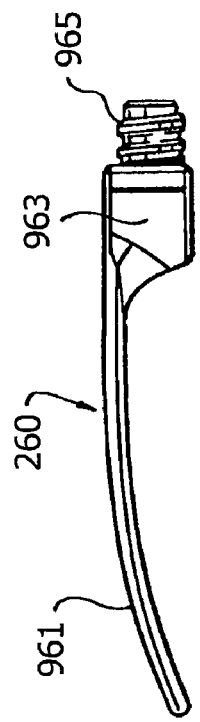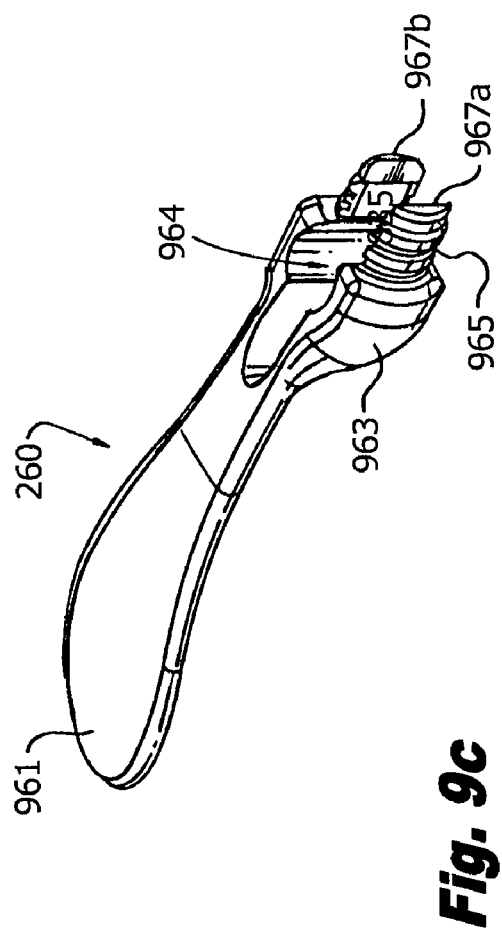

THERMAL MONITORING

CROSS-REFERENCE TO RELATED CASES

This application claims priority to, and the benefit of Provisional U.S. Patent Application Ser. No. 60/977,878, filed Oct. 5, 2007, the entirety of which is incorporated herein by reference.

TECHNICAL FIELD

This disclosure generally relates to monitoring a biological parameter after insertion of a medical device or a portion of a medical device into a body cavity and, more particularly, to a probe that allows for comfortable and easy insertion into the body cavity. A rectal thermal monitor (RTM) can be used to monitor temperature of the prostate gland, for example, during microwave or other therapies for treatment of benign prostatic hyperplasia (BPH).

BACKGROUND INFORMATION

The prostate gland is part of the male reproductive system, and consists of two lobes in front of the rectum, just below the bladder. The prostate gland surrounds the urethra, the channel through which urine passes out of the body. The prostate gland has two main periods of growth, the first of which occurs during puberty. However, during a man's mid-twenties, the prostate gland begins to grow again and continues to do so for the remainder of life. As the prostate gland grows, several problems often occur as a result of excessive growth. Rarely do such afflictions occur before the age of forty, but as a man's age increases, the likelihood of prostate gland afflictions increases significantly.

Benign prostatic hyperplasia (BPH) is the later growth of the prostate gland, which can cause symptoms such as pain, frequent urination and inability to fully empty one's bladder. Fortunately, a digital rectal exam can often lead to early detection of BPH, for which several effective treatment modalities exist. For example, drugs such as finasteride, transurethral microwave procedures, transurethral needle ablation, and surgical treatments are available.

Several approaches to treatment by heating the prostate are known. These approaches generally have difficulty in targeting the prostate without destroying healthy tissue. As a result, monitoring of the temperature of the prostate and surrounding areas is critical to safe and successful procedures. In order to measure accurately the rectal wall temperature and, thereby, monitor the prostate temperature, it is necessary that a probe of sufficient size be provided to press against the rectal wall at the appropriate location. However, probes of such size can cause pain and discomfort, at least upon insertion. Known techniques for monitoring internal temperature can provide not only poor performance but also discomfort during insertion.

SUMMARY OF THE INVENTION

The invention generally relates to thermal monitoring such as thermal monitoring with a rectal thermal monitor (RTM). The purposes and advantages of the invention will be set forth in and apparent from the description, drawings, and claims that follow. A probe according to the invention can be easily inserted into the body of a patient (human or other animal) and is comfortable for the patient during insertion, during a procedure with the probe within or partially within the patient, and during removal of the probe from the patient, while still effectively engaging an internal wall of the patient's body (such as the internal wall of the patient's rectum) after insertion into the patient's body.

In accordance with one aspect of the invention, a rectal thermal monitor for transrectal prostate temperature measurement includes a handle, an elongate shaft, a probe portion, and one or more temperature sensing elements. The handle is arranged in a proximal end portion of the monitor for gripping by a user, and the elongate shaft extends from the handle. The probe portion is arranged on a distal end portion of the shaft, at a position opposite the handle portion, and is shaped to facilitate insertion through an anal sphincter and into a rectum of a patient. The temperature sensing element is arranged within the distal probe portion, and is adapted and configured to sense the temperature of the prostate of the patient through the rectum wall of the patient. The temperature sensing elements can be supported by the shaft with a support element extending between the shaft and the temperature sensor.

Embodiments of this aspect or other aspects of the invention can include one or more of the following features. A cover element can be provided for covering at least a portion of the distal probe portion, the cover element comprising a resilient material. The temperature sensing element can therefore be arranged beneath the cover element. If desired, the probe portion can be overmolded onto the shaft. Additionally or alternatively, the temperature sensors can be insert molded into the probe portion. The probe portion can be made from any suitable compliant material, for example, from a material having a hardness of between about 10 and about 70 on the Shore A scale.

A tip portion can be arranged at a distal end of the probe portion to facilitate initial insertion of the monitor. The tip portion can be substantially rigid or can include a compliant, substantially non-compressible material. The average diameter of the tip portion can be substantially less than an average diameter of the probe portion. The temperature sensing element(s) can be attached to a heat sink to facilitate temperature measurement of an increased area. Additionally, the heat sink can be insert molded into the distal probe portion. Also, the heat sink can be supported by the shaft of the monitor by a rigid component extending between the shaft and the heat sink. The monitor can also include a stop, which is adapted and configured to be secured to the monitor, for preventing insertion of the monitor into the rectum of the patient beyond a predetermined point. The stop can be adjustably secured to the shaft. Further, the distal probe portion can include a tapered distal end to facilitate insertion through the anal sphincter.

The probe portion includes a compliant material, which is capable of compressing during insertion through the anal sphincter of the patient. Alternatively, or additionally, the probe can be formed so as to have one or more longitudinal channels defined in a surface thereof to facilitate compression of the probe.

In accordance with another aspect of the invention, a rectal thermal monitor for transrectal prostate temperature measurement includes a handle, an elongate shaft, a probe portion, and one or more temperature sensing elements. The handle is arranged in a proximal end portion of the monitor for gripping by a user, and the elongate shaft extends from the handle. The probe portion is arranged on a distal end portion of the shaft, at a position opposite the handle portion, and is shaped to facilitate insertion through an anal sphincter and into a rectum of a patient. The probe portion can include a compliant material having a hardness of between about 10 and about 70 on the Shore A scale. The temperature sensing element is arranged within the distal probe portion, and is adapted and configured to sense the temperature of the prostate of the patient through the rectum wall of the patient.

In accordance with still another aspect of the invention, a rectal thermal monitor for transrectal prostate temperature measurement includes a handle, an elongate shaft, a compressible probe portion, and one or more temperature sensing elements. The handle is arranged in a proximal end portion of the monitor for gripping by a user, and the elongate shaft extends from the handle. The compressible probe portion is arranged on a distal end portion of the shaft, at a position opposite the handle portion, and is shaped to facilitate insertion through an anal sphincter and into a rectum of a patient. The probe portion is provided on a rigid element separate from the shaft, which engages a distal end of the shaft to support the probe portion thereon. The temperature sensing element is arranged within the distal probe portion, and is adapted and configured to sense the temperature of the prostate of the patient through the rectum wall of the patient.

Embodiments of this aspect or other aspects of the invention can include one or more of the following features. The aforementioned rigid element extends distally past the probe portion and forms a distal tip at its distal end. The probe portion can include a compliant material, which is capable of compressing during insertion through the anal sphincter of the patient.

In accordance with a further aspect of the invention, a rectal thermal monitor for transrectal prostate temperature measurement includes a handle, an elongate shaft, a probe portion, and one or more temperature sensing elements. The handle is arranged in a proximal end portion of the monitor for gripping by a user, and the elongate shaft extends from the handle. The probe portion is arranged on a distal end portion of the shaft, at a position opposite the handle portion, and is shaped to facilitate insertion through an anal sphincter and into a rectum of a patient. The probe portion includes a compliant material, which is shaped so as to have one or more longitudinal channels formed in an outer surface thereof, to facilitate compression of the probe. The temperature sensing element is arranged within the distal probe portion, and is adapted and configured to sense the temperature of the prostate of the patient through the rectum wall of the patient.

In accordance with another aspect of the invention, a rectal thermal monitor for transrectal prostate temperature measurement includes a handle, a user-shapeable elongate shaft, a compressible probe portion, a cover element, and a temperature sensing element. The handle is arranged in a proximal end portion of the monitor for gripping by a user. The user-shapeable elongate shaft extends from the handle, and facilitates navigation of the anatomy of a patient. The probe portion is shaped to facilitate insertion through an anal sphincter and into a rectum of the patient. The cover element covers at least a portion of the distal probe portion, and is made from a resilient material. The temperature sensing element is arranged within the distal probe portion, beneath the cover element, and is adapted and configured to sense a temperature of the prostate of the patient through the rectum wall of the patient.

Embodiments in accordance with this or other aspects of the invention can include one or more of the following features. The shaft can extend past the distal probe portion to a distal end of the monitor, and/or the distal end of the shaft can terminate in a distal tip portion, to facilitate insertion through the anal sphincter of the patient.

In accordance with still another aspect of the invention, a method for inserting a rectal thermal monitor into a rectum of a patient includes providing a rectal thermal monitor in accordance with the invention, as set forth herein, aligning a distal end of the probe portion with the anal sphincter of the patient, urging the probe portion through the anal sphincter and into the rectum of the patient, and adjusting the rectal thermal monitor so that the to contact a portion of the rectum wall for which temperature is to be measured.

Both the foregoing summary and the following description are exemplary and not limiting.

BRIEF DESCRIPTION OF THE DRAWINGS

The accompanying drawings, which are incorporated in and constitute part of this specification, are included to illustrate and provide a further understanding of the invention. Together with the description, the drawings serve to explain the principles of the invention, wherein:

FIG. 4a is a top view of a portion of the RTM of FIG. 1;

FIG. 4b is a top view of a portion of the RTM of FIG. 1, having hidden lines to illustrate internal structure of the RTM;

FIG. 5a is a distal end view of the probe body portion of FIG. 1;

FIG. 5b is a cross-sectional view of the probe body portion of FIG. 1;

FIG. 5c is a top view of the probe portion of FIG. 1;

FIG. 5d is a cross-sectional view of the probe portion of FIG. 1;

FIG. 5e is a side view of the probe portion of FIG. 1;

FIG. 6c is a cross-sectional view of the probe portion of FIG. 6a;

FIG. 7a is an isometric view of an alternate embodiment of an end portion of a shaft of a RTM in accordance with the invention;

FIG. 7b is a top view of the end portion of FIG. 7a, having hidden lines illustrating internal structure;

FIG. 7c is a side cross-sectional view of the end portion of FIG. 7a;

FIG. 8a is a partial view of a temperature sensor assembly in accordance with the invention, showing a detail view of temperature sensors;

FIG. 8b is an isometric view of a temperature sensor assembly in accordance with the invention, having hidden lines illustrating internal structure;

FIG. 8c is a partial isometric view of a plug end of the temperature sensor assembly of FIG. 8b, having hidden lines illustrating internal structure;

FIG. 9a is a top view of a handle portion of an RTM, in accordance with the invention;

FIG. 9b is a side view of the handle of FIG. 9a;

FIG. 9c is a side isometric view of the handle of FIG. 9a;

DESCRIPTION

The devices and methods presented herein may be used in conjunction with any probe for which easy entry into and secure retention within a body cavity, such as the rectum is desired or required. The present invention is particularly suited for temperature measurement of the rectum wall of a patient during transurethral microwave dilatation (TUMD) for treatment of BPH.

Figure 1:
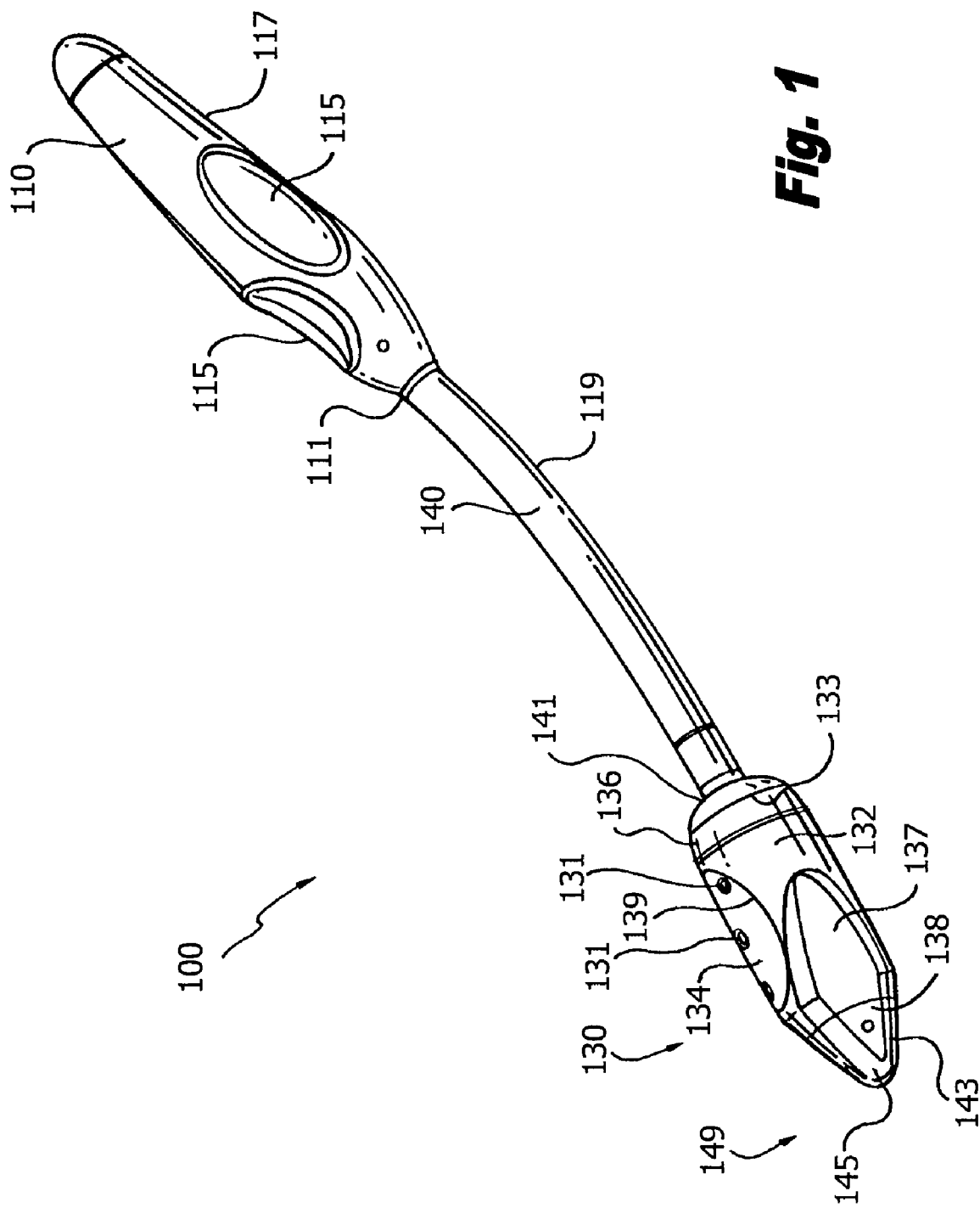
FIG. 1 is an isometric view of a representative embodiment of a rectal thermal monitor (RTM) in accordance with the present invention.

FIG. 1 illustrates a first embodiment of a rectal thermal monitor (RTM) in accordance with the invention, designated generally by reference number 100. The rectal thermal monitor 100 includes a handle portion 110, arranged at a proximal end portion, and a probe end 130 arranged at a distal end portion thereof. As illustrated, the handle is provided with a contour 117, to facilitate a secure and comfortable grip by a user, such as by a physician or technician. Detents 115 on one or more sides can be provided in order to facilitate engagement with the user's thumb, to help minimize slippage in the user's hand. Such detents can be provided with additional features, such as ridges, a compliant material, such as a silicone gel, and/or a rubberized surface to additionally prevent slippage and/or an otherwise textured surface.

A shaft 140 extends from a distal end 111 of the handle 110, and includes a contour 119, which facilitates insertion into and navigation of a patient's anatomy, allowing the operator to place the RTM 100 in the proper orientation with respect to the patient's prostate gland. The shaft 140 can be substantially rigid, and can be made from, for example, a molded plastic material. Alternatively, the shaft 140 can be made of a semi-rigid material, such as a rubber or other polymeric material. The shaft 140 can include a central core of a relatively more rigid material, such as, for example, polypropylene, with an outer sheath of silicone rubber for example.

The shaft 140, if embodied as a flexible shaft, can additionally or alternatively include a plurality of links, secured together at junctions with a predetermined coefficient of friction therebetween, so as to provide a desired amount of rigidity to the shaft 140 as a whole. Alternatively, the shaft can include multiple bundled strands therewithin that when shaped, friction between adjacent strands helps keep the probe end 130 in the adjusted position. Alternatively still, the shaft 140 can include a malleable material, such as a rubber or shape-memory polymer, but alternatively can be made of malleable metals such as aluminum or copper, for example. Alternatively still, the shaft 140 can be made of rigid, non-malleable acrylonitrile butadiene styrene (ABS), polypropylene or the like. If a polymer or other non-ferrous material is used, the rectal thermal monitor 100 can safely be used in an MRI field, if necessary. Alternatively still, the shaft 140 can include a material having open spaces, or slots formed therein, to allow the shaft 140 to flex along the desired axes. Such flexion, regardless of the precise implementation, can be provided about one axis, about two axes, or about an infinite number of axes.

The shaft 140, if embodied as a shapeable shaft, can be adjusted prior to commencement of insertion, or can be adjusted during insertion of the rectal thermal monitor 100. Such a capability enables the user (a physician or technician) to appropriately adjust the angle of the probe end 130 to fit the anatomy of the individual patient, thereby achieving firm contact between the rectum wall and the probe end 130, to obtain an accurate temperature reading.

The shaft 140 can additionally be provided with an expanded-diameter portion 141 at a point where the proximal end of the probe end 130 meets the shaft. This expanded-diameter portion 141, if provided, engages a proximal end 133 of the body 132 of the probe end 130, inhibiting proximal movement of the probe end 130, for example, during insertion of the RTM 100 into the rectum of a patient. Additional engagement elements can be provided, which will be described below in connection with other figures.

A probe end 130 is configured on a distal end portion of the shaft 140, or alternatively, secured to a distal end of the shaft 140. In the embodiment illustrated in FIG. 1, the shaft 140 continues through the probe end 130, ending in a distal tip 145. The tip 145 facilitates initial insertion through the anal sphincter of the patient. The tapered contour 143 of the tip 145 is continuous with one or more tapered regions 137 provided on the probe body 132. As such, the overall tapered contour of the probe end 130 facilitates easy and relatively comfortable insertion of the RTM 100 into the patient's rectum. Further, the probe body 132 can be compressible to facilitate easy and comfortable insertion. The probe body 132 can simply include a compressible or compliant material. Alternatively, the probe end 130 can include an internal structure that facilitates compression or "collapse" of the probe end, which will be discussed below in connection with FIGS. 6a-6c.

The tip 145 can, if desired, be more rigid than the remainder of the probe end 130. Accordingly, a different material can be used for the tip 145 than for the remainder of the body portion 132. A more rigid tip 145 can enable easier initial insertion of the rectal thermal monitor 100 through the anal sphincter of the patient. Since the diameter of the tip 145 is not very large, it will not cause any substantial discomfort to the patient, but will expedite the process of insertion. In alternative embodiments the more compliant materials of the body portion 132, including of the tapered region 137 can compress during insertion, while gently urging the anal sphincter open. When fully inserted, only the shaft 140 passes through the anal sphincter. Since the shaft 140 has a relatively small diameter, any patient discomfort is minimal.

As set forth above, the shape of probe end 130 facilitates insertion through the patient's anus and into the rectum. Once inserted, the convex shape of the probe end 130 roughly mirrors the general shape of the inner wall of the rectum, so that once the probe end 130 is in contact with the mucosa of the rectum wall, the probe end 130 is able to contact a substantial area thereof, in order to obtain an accurate temperature reading of the prostate gland through the rectum wall.

Figure 2:
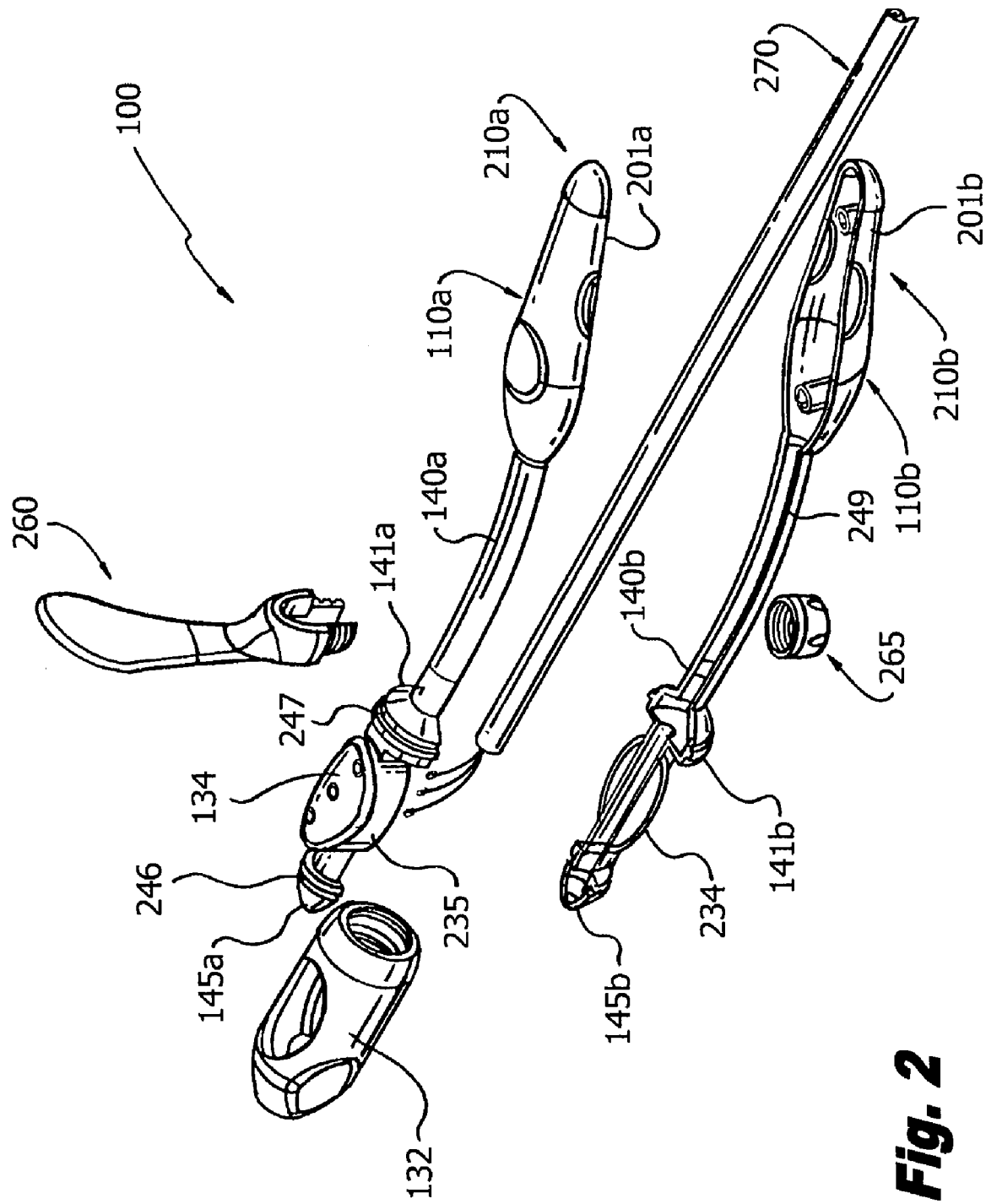
FIG. 2 is an exploded view of the RTM of FIG. 1.

One or more temperature sensors 131 are provided in the probe end 130 of the RTM 100. The temperature sensor(s) 131 can be any suitable type, such as one or more thermocouples, and/or one or more thermistors, for example. The temperature sensor(s) 131, are optionally provided in a heat sink 134. Alternatively or additionally, the temperature sensor(s) 131 can be welded to the heat sink 134. The heat sink 134 and/or the temperature sensors 131 can be insert molded into the probe end 130. Alternatively, the heat sink 134 and/or temperature sensors 131 can be supported directly from the shaft 140, or an extension thereof, as can be seen in FIG. 2, for example. As set forth above, the temperature sensors can be thermocouples, thermistors or alternatively another type of temperature sensor that effectively measures temperature.

For example, non-contact type temperature sensors, such as those that measure temperature based on measurement of infra-red radiation, can be used.

In the embodiment of FIG. 1, the probe body 132 includes an aperture 139, the edge of which contacts the heat sink 134. A proximal portion 136 of the probe body 132 includes a contour that is continuous with a contour of the expanded-diameter portion 141. As set forth above, contours of the tapered regions, such as tapered region 137 of the body 132, are continuous with the contour of the distal tip 145, even though they are, in this embodiment, separate pieces with the distal end 138 of the probe body 132 abutting the tip 145 along interface 149. In alternative embodiments, the tip 145 can be part of the probe body 132, constructed as a single piece. In such embodiments, a rigid or semi-rigid core can be provided, if desired, to impart additional structure to the probe body 132 and tip 145.

A portion of, or the entire rectal thermal monitor 100, as with other embodiments set forth hereinbelow, can be overmolded (not shown) with a layer of resilient material, such as a thermoplastic elastomer (TPE), silicone rubber or the like. Such overmolded cover can include a relatively low coefficient of friction, in contact with the mucosa of the patient, allowing even easier and still more comfortable insertion. Additionally, such cover protects the components of the RTM 100, and imparts impermeability to the RTM 100, in addition to more effective sanitization or sterilization. However, if the probe body 132 fits closely with the heat sink 134 or is directly molded thereto, such as by insert molding, an effective RTM can be achieved, even without the use of an additional cover element.

The rectal thermal monitor 100 can be composed primarily from polymeric materials, although components can include metals such as steel, copper, aluminum, alloys, shape-memory alloys, and/or composite materials as desired or required. The handle 110 can include a material or covering of material that enhances gripping by the user, and the probe end 130 can include a material, or covering of material that provides relatively low coefficient of friction against a patient's anatomy, to facilitate easy insertion, as set forth above. A relatively rigid overall structure can be provided, so that the probe end 130 can be effectively inserted and accurately oriented with respect to the patient's anatomy. However, the probe end 130 itself can include a layer of compliant material, such as silicone, beneath the outer covering. Additionally or alternatively, silicone, thermoplastic elastomer, rubber, thermosetting plastics, thermoplastic materials having a hardness of between 10 and 70 on the shore A scale, or any value therebetween, can be used. Such materials can be directly molded onto the shaft by way of an insert molding process, if so-desired. The probe end 130 alternatively can be made wholly or in part, from a compliant material such as silicone rubber or foam rubber. In such an instance, a more rigid portion can be incorporated within the probe end 130 to provide rigidity the probe end 130. Polymers such as Nylon, polyethylene terephthalate (PET), or acrylonitrile butadiene styrene (ABS) can be used for relatively rigid components of the rectal thermal monitor 100.

The rectal thermal monitor 100 can be sized such that it is both large enough to perform the necessary tasks, and small and light enough to prevent user fatigue and patient discomfort. The shaft 140 can be long enough so that the probe end 130 can be situated within the patient's rectum, while the handle portion 110 remains external to the patient with the stop 260 (FIG. 2) acting as a guide, and to prevent excessive insertion into the patient's rectum. Depending on the precise implementation of the invention, the probe end 130, when in a position for measurement of temperature, is about 2.5 inches (6.25 cm) in length and about 0.5 inches (1.25 cm) in diameter. The rectal thermal monitor 100, as a whole, can be about 12 inches (30 cm) in length. Naturally, depending on the specific needs or desires, these dimensions can be chosen accordingly. The stop 260 (FIG. 2) can be about one inch (2.5 cm) in length, or another length that is effective to prevent excessive insertion of the rectal thermal monitor 100, without unnecessarily interfering with necessary manipulation of the rectal thermal monitor 100.

If desired, the rectal thermal monitor 100 can be manufactured in a range of sizes for different sizes of patient. For a larger patient, it may be necessary to provide a longer shaft, and/or to increase the size of the probe end.

In accordance with the invention, the handle portion 110 can be sized such that it is noticeably larger than the probe end 130, in order to give the illusion of smaller probe end 130. Accordingly, patient anxiety can be reduced, in comparison with use of a probe that the patient conceives is large. Additionally or alternatively, colors for the probe end 130 can be selected to minimize the apparent size of the probe end 130. For example, the probe end 130 can be fabricated from a dark-colored material, such as black, dark blue, or dark green. Similarly, a pattern of different colors can be utilized. For example, the probe end 130 can be provided with alternating regions of dark and light colors, in order to visually break-up the shape of the probe end 130. A similar approach can be taken in coloring or patterning the entire rectal thermal monitor 100, including the shaft 140 and the handle 110.

In use, the physician or technician inserts the probe end 130 of the rectal thermal monitor 100 into the anus of the patient and orients the rectal thermal monitor 100 such that the temperature sensor(s) 131 is/are in a position with respect to the rectum wall such that the temperature of the prostate gland can be monitored. An inserter or sleeve, as will be described below can also be used to facilitate insertion of the rectal thermal monitor 100. Further, FIGS. 11 and 12 respectively illustrate a RTM 100 in accordance with the invention traversing the anal canal A of a patient, and inserted into the rectum R of a patient, arranged in a position to sense the temperature of the prostate gland P through the wall of the rectum R.

Upon completion of the procedure, the rectal thermal monitor 100 can be configured so that the probe end compresses during withdrawal. The tapered contour of the proximal region 136 of the probe body 132 can facilitate compression during withdrawal in conjunction with the patient anatomy.

FIG. 2 is an exploded view of the RTM 100 of FIG. 1. Included in this illustration is a stop 260 that is provided on the shaft 140 of the rectal thermal monitor 100. The stop 260 acts as a guide to the user, to prevent the RTM 100 from being inserted excessively into the rectum. The stop 260 can be fixed relative to the body of the rectal thermal monitor 100, or can be adjustably secured thereto with, for example, a friction fit, snap fit, locking clip, thumbscrew, or other adjustable locking component. In the embodiment illustrated, the stop 260 is adjustably secured to the shaft 140, using a nut 265. The nut 265 secures to the stop 260, and effectively clamps the stop 260 to the shaft 140 by compressing the shaft 140 between the nut 265 and the stop body.

As illustrated, the body of the RTM 100, including the handle 110, shaft 140, expanded diameter portion 141 and distal tip 145, is divided along a midline into upper and lower parts 210a and 210b. This results in the division of the handle 110 into upper and lower parts 110a, 110b, the shaft 140 into upper and lower parts 140a, 140b, the expanded diameter portion 141 into upper and lower parts 141a, 141b and the distal tip 145 into upper and lower parts 145a, 145b. Each of the parts 210a, 210b of the RTM 100 joins the other along respective faces 201a, 201b. Separation of the upper and lower parts 210a, 210b allows easy insertion of a temperature sensor assembly 270 through a channel 249 formed between the two parts 210a, 210b. It is to be understood that although the RTM 100 is illustrated as including component parts separable in one manner, that the parts can be separated in another manner, depending on the precise implementation. Such parts can be joined together by snap fit, mechanical fasteners such as clips or screws, by adhesive or by welding, such as by heat, RF, ultrasonic or solvent welding.

FIG. 2 also illustrates that the probe end 132 can be embodied such that it engages protrusions 246, 247 formed on the shaft 140 at the tip 145 and at the expanded-diameter portion 141. As can be seen in FIG. 5b, matching grooves can be formed on the inner surface of the probe body 132. Further, as can be seen, the heat sink 134 can be mounted on a standoff 235 formed in the upper half 210a of the RTM 100. A lower plate 234 can be formed on the lower body half 210b, to enclose the wires of the temperature sensor assembly 270, within a protected housing.

Figure 3A:
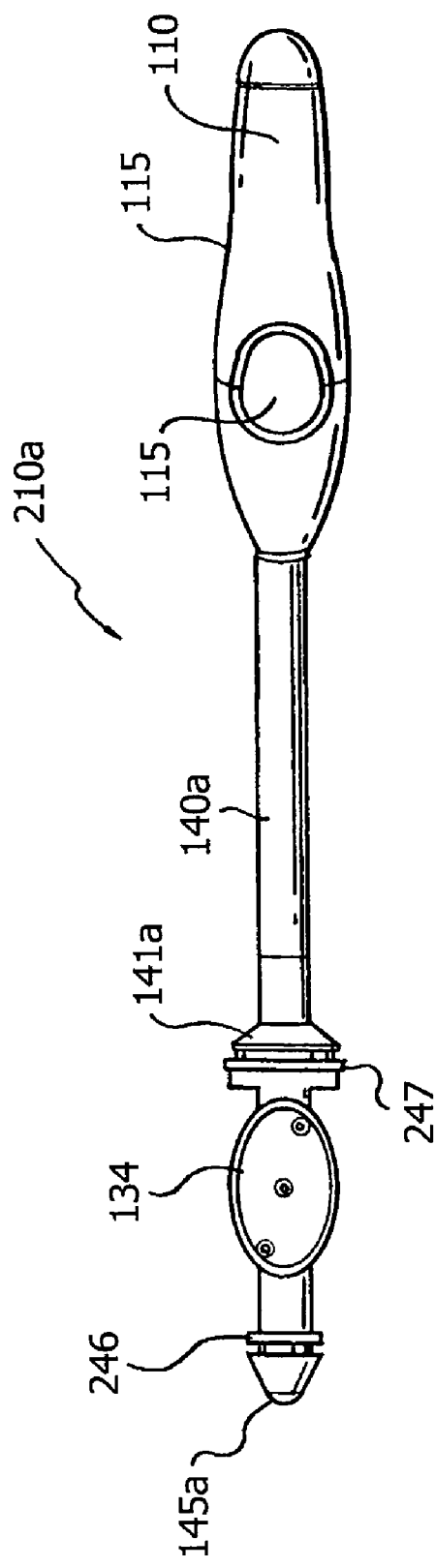
FIG. 3a is a top view of an upper portion of the RTM of FIG. 1, with a probe body portion removed from a shaft of the RTM.
Figure 3B:
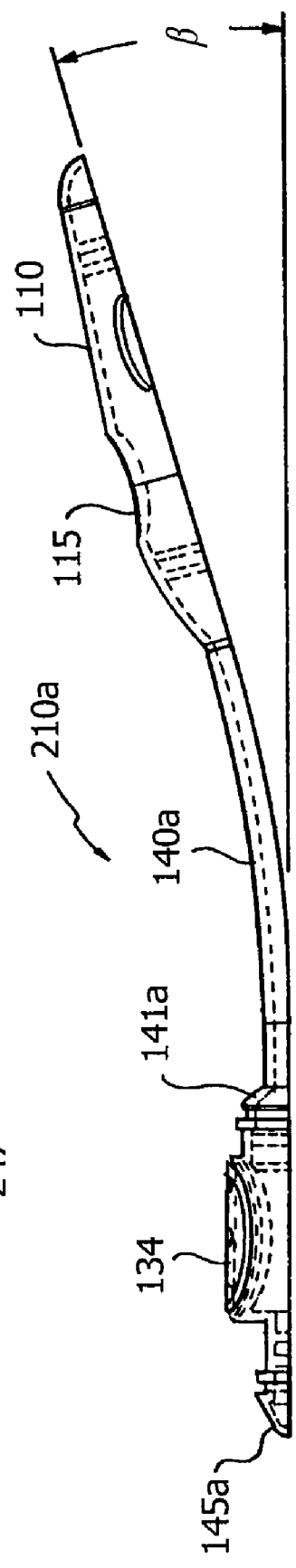
FIG. 3b is a side view of the upper portion of the RTM of FIG. 1, with a probe body portion removed from a shaft of the RTM.

FIGS. 3a and 3b are top and side views of the upper half 210a of the RTM 100. From the side view of FIG. 3b, the curvature of the shaft 140 of the RTM 100 is apparent. Specifically, the surface of the heat sink 134, which represents the outer surface of the probe end 130, which is inserted into the rectum of a patient, is arranged at an angle, beta (β), with respect to the center line of the handle 110. Such angle can be as slight or as extreme as desired, to facilitate insertion and orientation of the probe end 130 of the RTM 100. This angle, beta (β), can range from about 0 to about ±75 degrees, and can be any angle therebetween, at one-degree increments, inclusive. In one embodiment, the angle, beta (β), is about 17 degrees.

FIGS. 4a and 4b are top views of a RTM half 401, in which the RTM 100 has been divided lengthwise along a line, 90-degrees from the division line of FIGS. 2 and 3a-3b, with respect to the central axis of the RTM 100. FIG. 4b illustrates internal structure by including dashed lines representing hidden lines. The orientation of the longitudinal channel shown in FIG. 2 is visible, for example.

FIGS. 5a-5e illustrate various views of a probe end body 132, in accordance with the invention, and as illustrated, for example, in FIGS. 1 and 2. The aperture 139, for accepting a heat sink, e.g., heat sink 134, is shown, which communicates with a cavity 538. This cavity accepts the heat sink 134, as well as a shaft portion, which extends between the expanded-diameter portion 141 and the distal tip 145. As set forth above, a temperature sensor assembly 270, which includes a cable having conductors, can also pass through the cavity 538.

Also visible in FIGS. 5a-5e are grooves 543, 545 for engaging protrusions on the shaft 140 of the RTM 100. Finally, left and right contoured regions 137a, 137b are seen, which help facilitate insertion of the probe end 130. The left and right contoured regions 137a, 137b are angled, with respect to the main outer surface of the probe body 132, at an angle alpha (α). This angle, alpha (α), can range from between 0 and 90 degrees, and can be any angle therebetween, at one-degree increments, inclusive. In one embodiment, alpha (α) is about 28 degrees. An upper contour 536 and a concave lower contour 239 are also illustrated, each of which reduces the profile of the probe body 132, to ease insertion thereof. A lower distal contour 537 forms a continuous contour with the tip portion 145, when installed thereon. Naturally, other shapes for a probe body 132 are possible without departing from the spirit of the invention.

Figure 6A:
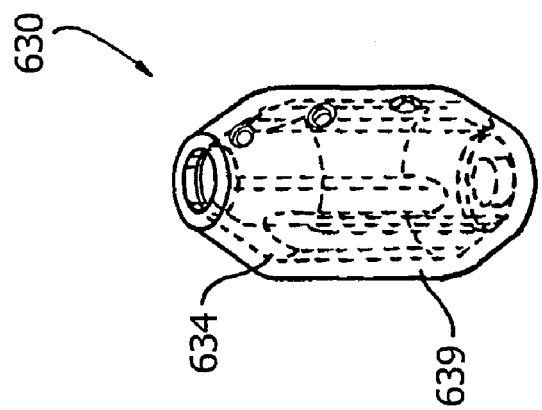
FIG. 6a is an isometric view of an alternate probe body portion in accordance with the invention, having hidden lines illustrating internal structure.
Figure 6B:
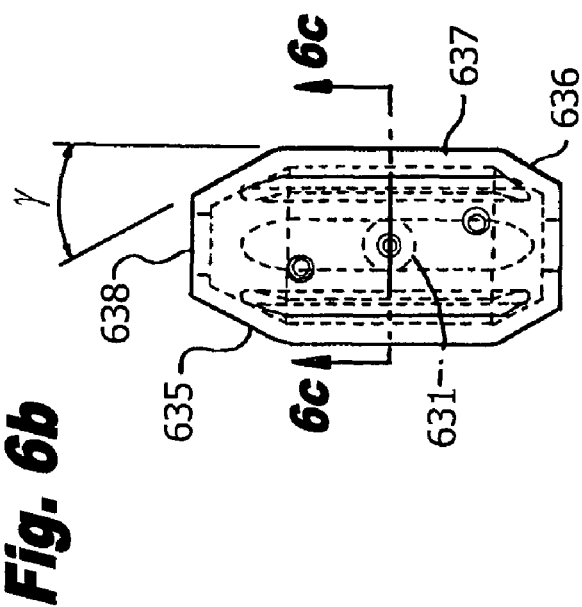
FIG. 6b is a side view of the probe portion of FIG. 6a, having hidden lines illustrating internal structure.
Figure 6C:
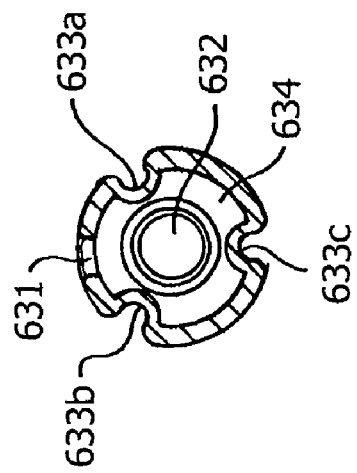

FIGS. 6a-6c illustrate one alternate embodiment for a probe end 630, in accordance with the invention. FIG. 6a is an isometric view of the probe end 630, having hidden lines to show internal structure. The probe end 630 includes a core 634 and a covering. One or more temperature sensors 631 are also provided. A distal end portion 635 is provided, and is angled to ease insertion. The angle of the end portion 635, with respect to the middle portion 637 is indicated by angle gamma (γ). The angle is analogous to alpha (α) of FIG. 5c, and in one embodiment gamma (γ) is about 28 degrees. However, the angle, gamma (γ), can range from between 0 and 90 degrees, and can be any angle therebetween, at one-degree increments, inclusive.

As can best be seen in the cross-section of FIG. 6c, a hollow channel 632 is also formed therethrough, to allow passage of cables of the temperature sensor assembly 270. More importantly, however, the cross-sectional shape of the core portion 634 is clearly visible. The core 634 includes a plurality of channels 633a-633c, which are formed lengthwise in the outer surface of the core 634. These channels 633a-633c can allow the probe end 630 to compress more easily, because the material of the core 634 can expand circumferentially into the regions defined by the channels 633a-633c, while compressing radially. In effect, the channels 633a-633c allow the core 634 to collapse on itself during compression. Accordingly, less compression of the material itself is necessary, and therefore, less effort during insertion is required. Since the outward force exerted by the probe end 630 is therefore also less, patient discomfort can additionally be minimized by use of this embodiment.

In alternative embodiments, the channels can be provided in any number. One, two, four, five, six, seven or more channels can be arranged and sized so as to provide the desired structural characteristics and compliance. Additionally or alternatively, the channels can be formed within the core 634, or probe end alone if provided without a cover 639. That is, channels need not be formed in the surface of the probe or core 634, but can be hidden from view, within the body of the probe end.

In the embodiment of FIGS. 6a-6c, the cover 639 covers the core 634, and therefore also bridges across the channels 633a-633c, giving the appearance of a continuous probe end 630. The cover 639 also facilitates the relative circumferential movement of material of the core 634 into the spaces defined by the channels 633a-633c, during the longitudinal movement of the RTM through the anal sphincter of the patient.

FIGS. 7a-7c illustrate an alternate embodiment of a distal end portion of a shaft, for use in RTMs in accordance with the invention. Particularly, the shaft end portion 740 is configured to connect, by way of resilient latches 743 to a shaft of a RTM. This allows for attachment of a probe body (e.g., probe body 132) and subsequent attachment of the shaft end portion 740 to a shaft. A protrusion 745 is provided, which acts as a stop to prevent excessive insertion of the end portion 740 into another shaft. A tip portion 145 is provided on the shaft end portion 740, and a channel 747 (FIG. 7c) is formed therein, which communicates at a top surface with a lengthwise aperture 741, and at the other end with a proximal aperture 742. A probe end can be inserted onto the shaft end portion 740, which can then be inserted onto a shaft and/or handle of the remainder of a RTM in accordance with the invention.

FIGS. 8a-8c illustrate a temperature sensor assembly 800 (FIG. 8b), a detail view of temperature sensor connections (FIG. 8a), and a detail view of a plug end (FIG. 8c), respectively. The temperature sensors 831 are attached to insulated conductors 835, which are bundled and pass through an insulating and protective sheath 810. The conductors each terminate at respective pins 853 held by a plug 850. The temperature sensors 831, as set forth above, are placed within a probe portion, and can be held within a heat sink in the probe portion. The plug 850, which is at one end of a long cord, connects with treatment equipment, with raw temperature data being sent from the RTM to the treatment equipment.

Figure 10B:
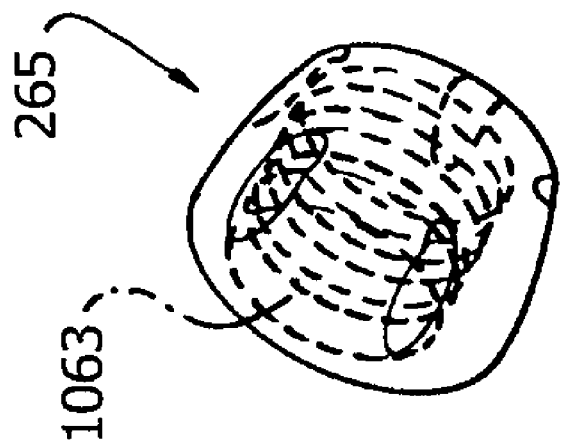
FIG. 10b is an isometric view of the nut of FIG. 10a, having hidden lines illustrating internal threads thereof.
Figure 10A:
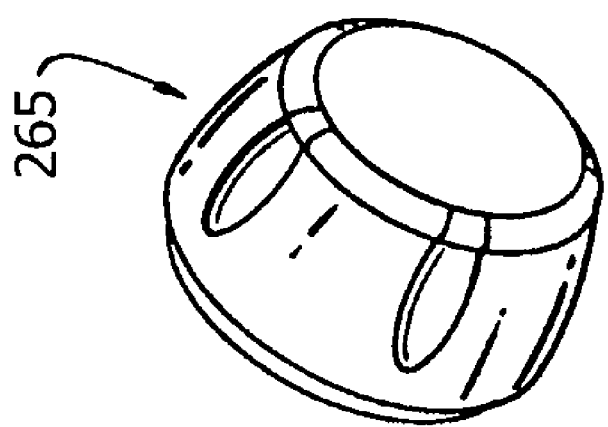
FIG. 10a is an isometric view showing an exterior surface of a nut for securing the handle of FIG. 9a to a RTM in accordance with the invention.

FIGS. 9a-9c illustrate the stop 260 of FIG. 2 in further detail. FIGS. 10a and 10b illustrate the nut 265 of FIG. 2 in additional detail, which nut 265 engages the threads 965 of the stop 260. The stop includes a main body portion 961, which effectively abuts the buttocks of a patient to prevent excessive insertion of RTMs in accordance with the invention, and to act as a guide. A shaft of a RTM in accordance with the invention is received by a channel 964 formed in an expanded-thickness portion 963 of the stop 260. The nut 265 of FIG. 10a and 10b is screwed onto the threads 965 of the stop 260, which are engaged by the threads 1063 of the nut 265. Tightening of the nut 265 causes the free ends 967a, 967b of the threaded portion to move toward one another, causing the channel 964 to tighten around and clamp onto the shaft of the RTM.

Figure 11:
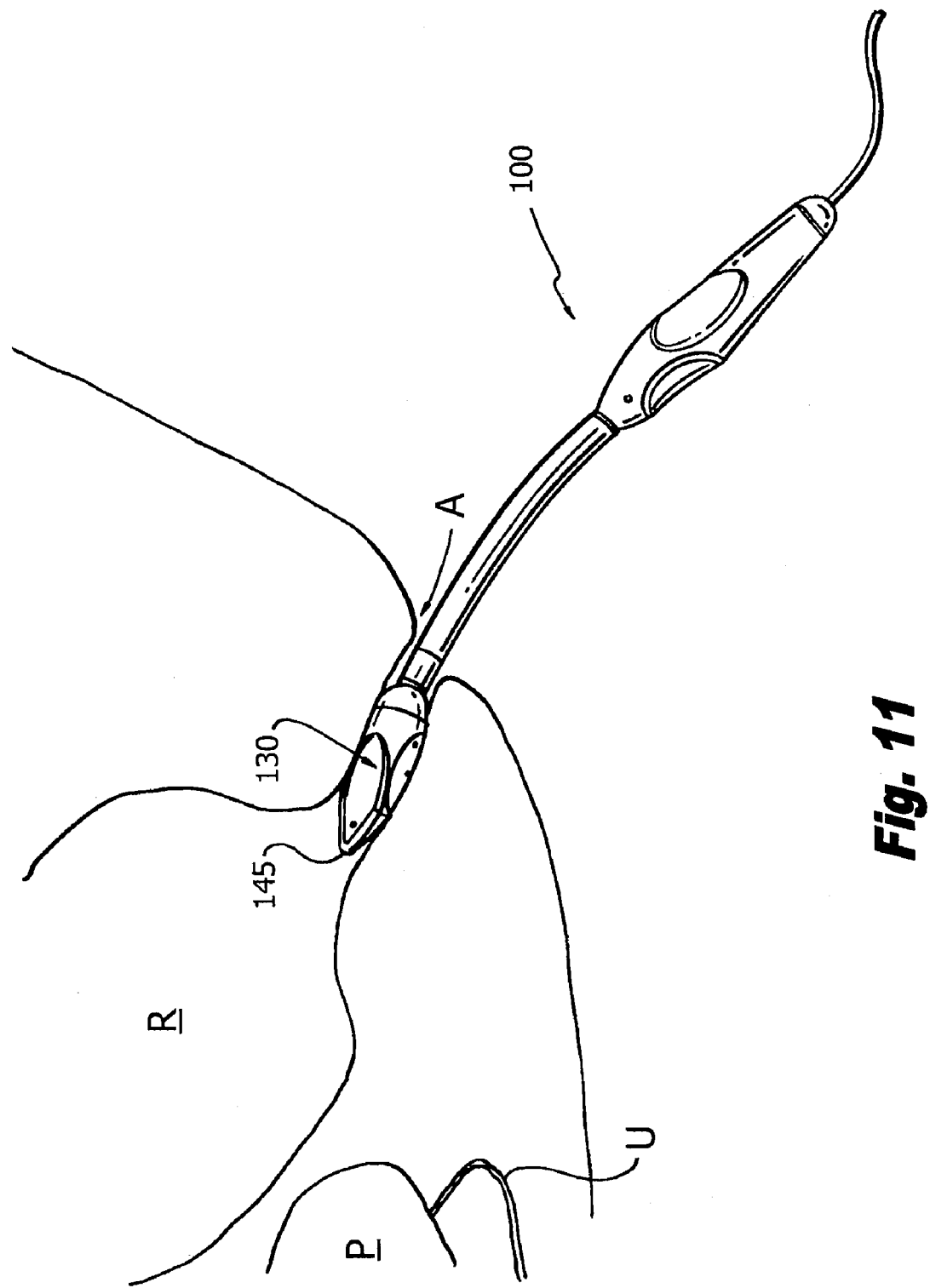
FIG. 11 is an illustration showing a RTM in accordance with the invention traversing the anal canal of a patient, during insertion of the RTM.

FIG. 11, as discussed briefly above, is an illustration showing a RTM 100 in accordance with the invention traversing the anal canal A of a patient, during insertion of the RTM 100. While the anal sphincter must necessarily expand to allow passage of the probe end 130, the degree of opening can be reduced by imparting some degree of compressibility to the probe end 130 as described herein. Further, a tip 145, as describe above, aids in initial insertion of the RTM 100 through the anal sphincter.

Figure 12:
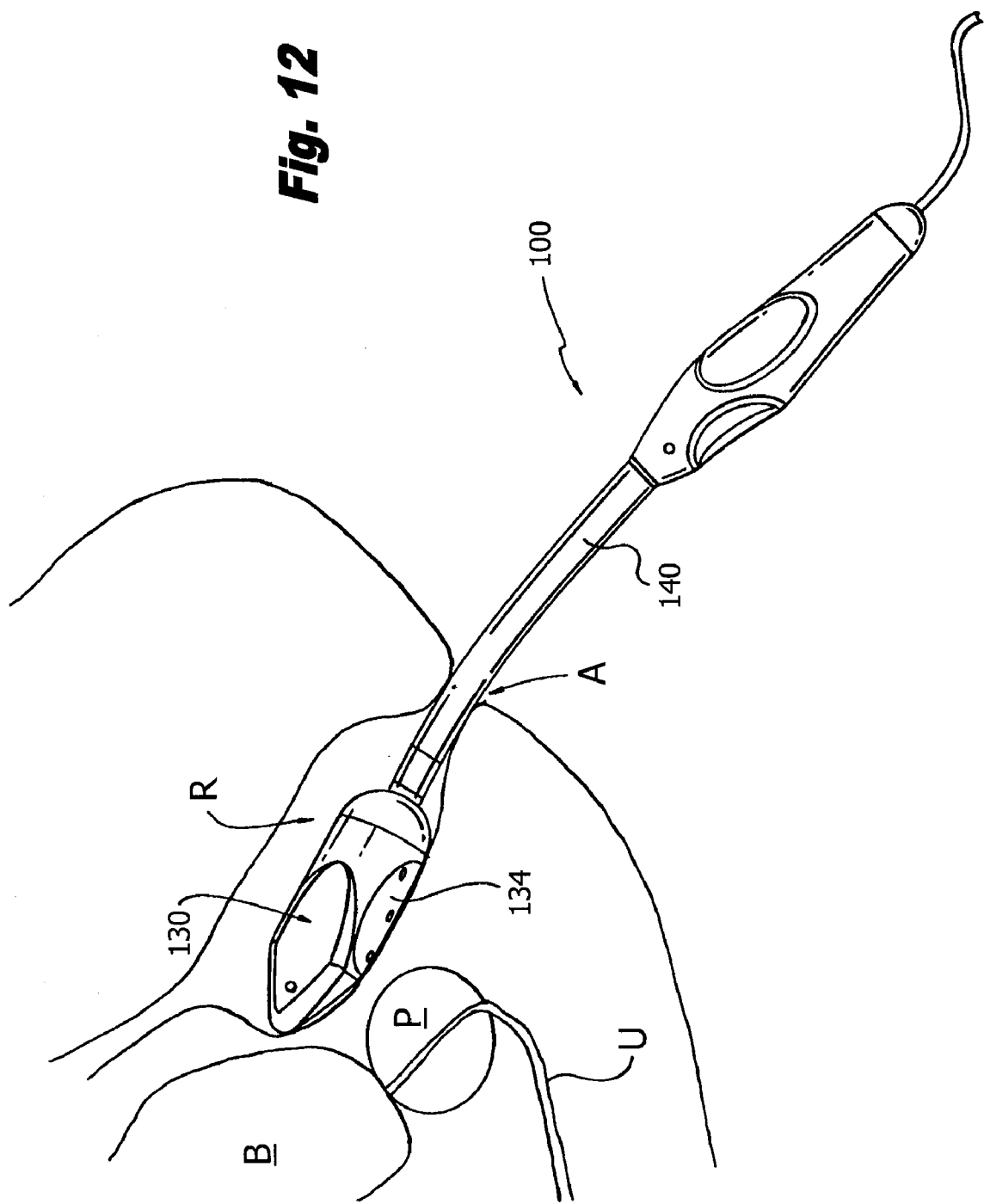
FIG. 12 is an illustration showing a RTM in accordance with the invention, inserted into the rectum of a patient, arranged in a position to sense the temperature of the prostate gland through the rectum wall.

FIG. 12, as mentioned above, is an illustration showing a RTM 100 in accordance with the invention, inserted into the rectum R of a patient, and arranged in a position to sense the temperature of the prostate gland P through the wall of the rectum R. The relative position of the heat sink 134 with respect to the prostate gland P and urethra U is seen. The bladder B is also shown for context. As can be seen, the rectum wall and probe end 130 conform to each other, when placed adjacently to one another. The shaft 140 is the only component of the RTM 100 passing through the anal canal A, during temperature measurement.

Further, RTMs in accordance with the present invention can be utilized in conjunction with sleeves to facilitate insertion thereof. Such sleeves are first inserted through the anal sphincter of a patient, prior to insertion of a RTM. As the probe traverses the length of the sleeve, the probe end is compressed, such that it fits more easily into the rectum of the patient. Insertion can be eased, in comparison with insertion without the use of such a sleeve, because longitudinal forces against the anal sphincter are essentially eliminated, leaving only radially outward forces to urge the anal sphincter open, which can greatly reduce patient discomfort.

At least some of the disclosed embodiments according to the invention relate to rectal thermal monitors and accessories therefore that can effectively sense the temperature of the rectum wall, while still enabling relatively easy and less painful insertion, minimizing discomfort to the patient. Various features of the disclosed embodiments can be changed, deleted, and/or mixed in various combinations even if not expressly disclosed herein. This disclosure is exemplary and not limiting.

What is claimed is:

1. A rectal thermal monitor for transrectal prostate temperature measurement, comprising:

(a) a handle arranged in a proximal end portion of the monitor for gripping by a user;
(b) an elongate shaft extending from the handle, the elongate shaft capable of being bent into a shape by the user and of retaining the shape prior to insertion into a patient;
(c) a probe portion having a first diameter arranged on a distal end portion of the shaft, at a position opposite the handle portion, shaped to facilitate insertion through an anal sphincter and into a rectum of the patient, the probe portion including a plurality of channels radially disposed along an outer surface of the probe portion and extending between a proximal end and a distal end of the probe portion, the channels configured to cause compression of the probe portion to a second smaller diameter when the probe portion passes through the anal sphincter; and
(d) a temperature sensing element arranged within the distal probe portion, adapted and configured to sense a temperature of the prostate of the patient through the rectum wall of the patient, the temperature sensing element being supported by the shaft of the monitor by a support extending between the shaft and the temperature sensor.

2. The monitor of claim 1 further comprising a cover element covering at least a portion of the distal probe portion, the cover element comprising a resilient material, the temperature sensing element being arranged beneath the cover element.

3. The monitor of claim 1 wherein the probe portion is overmolded onto the shaft.

4. The monitor of claim 1 wherein the probe portion comprises a material having a hardness between about 10 and 70 on the Shore A scale.

5. The monitor of claim 1 further comprising a tip portion arranged at a distal end of the probe portion to facilitate initial insertion of the monitor into the patient.

6. The monitor of claim 5 wherein the tip portion is substantially rigid.

7. The monitor of claim 5 wherein the tip portion includes a complaint material.

8. The monitor of claim 5 wherein an average diameter of the tip portion is substantially less than an average diameter of the probe portion.

9. The monitor of claim 5 wherein the tip portion includes a non-compressible material.

10. The monitor of claim 1 wherein the temperature sensing element is attached to a heat sink to facilitate temperature measurement of an increased area, and wherein the heat sink is insert molded into the distal probe portion.

11. The monitor of claim 10 wherein the heat sink is supported by the shaft of the monitor by a rigid component extending between the shaft and the heat sink.

12. The monitor of claim 1 further comprising a stop, adapted and configured to be secured to the monitor, for preventing insertion of the monitor into the rectum of the patient beyond a predetermined point.

13. The monitor of claim 12 wherein the stop is adjustably secured to the shaft.

14. The monitor of claim 1 wherein the probe portion includes a tapered distal end to facilitate insertion through the anal sphincter.

15. A rectal thermal monitor for transrectal prostate temperature measurement, comprising:

(a) a handle arranged in a proximal end portion of the monitor for gripping by a user;

(b) an elongate shaft extending from the handle, the elongate shaft capable of being bent into a shape by the user and of retaining the shape prior to insertion into a patient;

(c) a probe portion having a first external circumference and being arranged on a distal end portion of the shaft, at a position opposite the handle portion, shaped to facilitate insertion through an anal sphincter and into a rectum of the patient, the probe portion including a plurality of channels radially disposed along an outer surface of the probe portion and extending between a proximal end and a distal end of the probe portion, the channels configured to cause compression of the probe portion to a second smaller circumference when the probe portion passes through the anal sphincter; and (d) a temperature sensing element arranged within the distal probe portion, adapted and configured to sense a temperature of the prostate of the patient through the rectum wall of the patient.

16. The monitor of claim 15 wherein the probe portion includes a compliant material having a hardness of between about 10 and about 70 on the Shore A scale.

17. A rectal thermal monitor for transrectal prostate temperature measurement, comprising:

(a) a handle arranged in a proximal end portion of the monitor for gripping by a user;

(b) an elongate shaft extending from the handle, the elongate shaft capable of being bent into a shape by the user and of retaining the shape prior to insertion into a patient;

(c) a probe portion arranged on a distal end portion of the shaft, at a position opposite the handle portion, shaped to facilitate insertion through an anal sphincter and into a rectum of the patient, the probe portion being provided on a rigid element separate from the shaft, the rigid element engaging a distal end of the shaft to support the probe portion thereon, the probe portion including a plurality of channels radially disposed along an outer surface of the probe portion and extending between a proximal end and a distal end of the probe portion, the channels configured to flex transversely and cause compression of the probe portion when the probe portion passes through the anal sphincter; and (d) a temperature sensing element arranged within the distal probe portion, adapted and configured to sense a temperature of the prostate of the patient through the rectum wall of the patient.

18. The monitor of claim 17 wherein the rigid element extends distally past the probe portion and forms a distal tip at its distal end.

19. A rectal thermal monitor for transrectal prostate temperature measurement, comprising:

(a) a handle arranged in a proximal end portion of the monitor for gripping by a user;

(b) an elongate shaft extending from the handle, the elongate shaft capable of being bent into a shape by the user and of retaining the shape prior to insertion into a patient;

(c) a probe portion shaped to facilitate insertion through an anal sphincter and into a rectum of the patient, the probe portion including a plurality of channels radially spaced about an outer surface of the probe portion and extending between a proximal end and a distal end of the probe portion, the channels configured to flex to cause compression of the probe portion when the probe portion passes through the anal sphincter;

(d) a cover element, covering at least a portion of the distal probe portion, the cover element being made from a resilient material; and (e) a temperature sensing element arranged within the distal probe portion, beneath the cover element, adapted and configured to sense a temperature of the prostate of the patient through the rectum wall of the patient.

20. The monitor of claim 19 wherein the shaft extends past the distal probe portion to a distal end of the monitor.

21. The monitor of claim 20 wherein the distal end of the shaft terminates in a distal tip portion to facilitate insertion through the anal sphincter of the patient.

22. A method of inserting a rectal thermal monitor for transrectal prostate temperature measurement into a rectum of a patient, the method comprising:

(a) providing a rectal thermal monitor comprising:

(i) a handle arranged in a proximal end portion of the monitor for gripping by a user;

(ii) an elongate shaft extending from the handle, the elongate shaft capable of being bent into a shape by the user and of retaining the shape prior to insertion into a patient;

(iii) a probe portion arranged on a distal end portion of the shaft, at a position opposite the handle portion, shaped to facilitate insertion through an anal sphincter and into a rectum of the patient, the probe portion including a plurality of channels radially spaced about an outer surface of the probe portion and extending between a proximal end and a distal end of the probe portion, the channels configured to flex and to cause compression of the probe when the probe portion passes through the anal sphincter;

(iv) a cover element, covering at least a portion of the distal probe portion, the cover element being made from a resilient material; and (v) a temperature sensing element arranged within the distal probe portion, beneath the cover element, adapted and configured to sense a temperature of the prostate of the patient through the rectum wall of the patient, the temperature sensing element being supported by the shaft of the monitor by a support extending between the shaft and the temperature sensor;

(b) aligning a distal end of the probe portion with the anal sphincter of the patient;

(c) urging the probe portion through the anal sphincter and into the rectum of the patient; and (d) adjusting the rectal thermal monitor to contact a portion of the rectum wall for which temperature is to be measured.

* * * * *